United States Patent
Liu et al.

(10) Patent No.: US 10,646,534 B2
(45) Date of Patent: May 12, 2020

(54) FORMULATION, PREPARATION METHOD AND USE OF CHINESE HERBAL MEDICINE COMPOSITION FOR SOOTHING LIVER

(71) Applicant: INFINITUS (CHINA) COMPANY LTD., Jiangmen, Guangdong (CN)

(72) Inventors: Shuo Liu, Guangdong (CN); Huawei Zhu, Guangdong (CN); Yiting Yang, Guangdong (CN); Chung Wah Ma, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 351 days.

(21) Appl. No.: 15/529,381

(22) PCT Filed: Jan. 20, 2017

(86) PCT No.: PCT/CN2017/071953
§ 371 (c)(1),
(2) Date: May 24, 2017

(87) PCT Pub. No.: WO2017/101889
PCT Pub. Date: Jun. 22, 2017

(65) Prior Publication Data
US 2018/0028588 A1    Feb. 1, 2018

(30) Foreign Application Priority Data
Dec. 15, 2015 (CN) ............................ 2015 1 0938258

(51) Int. Cl.
| | | |
|---|---|---|
| *A61K 36/89* | (2006.01) | |
| *A61K 36/752* | (2006.01) | |
| *A61K 36/82* | (2006.01) | |
| *A61K 36/232* | (2006.01) | |
| *A61K 36/236* | (2006.01) | |
| *A61K 36/8905* | (2006.01) | |
| *A61K 36/71* | (2006.01) | |
| *A61K 9/16* | (2006.01) | |
| *A61K 9/00* | (2006.01) | |
| *A61K 36/65* | (2006.01) | |

(52) U.S. Cl.
CPC ............ *A61K 36/89* (2013.01); *A61K 9/0053* (2013.01); *A61K 9/1688* (2013.01); *A61K 36/232* (2013.01); *A61K 36/236* (2013.01); *A61K 36/65* (2013.01); *A61K 36/71* (2013.01); *A61K 36/752* (2013.01); *A61K 36/82* (2013.01); *A61K 36/8905* (2013.01); *A61K 2236/30* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 7,662,412 B2 * | 2/2010 | Guo | ..................... | A61K 36/258 |
| | | | | 424/725 |
| 2003/0100544 A1 | 5/2003 | Scherlitz-Hofmann et al. | | |
| 2012/0029070 A1 * | 2/2012 | Yamamoto | ........... | A61K 9/1623 |
| | | | | 514/473 |
| 2012/0315332 A1 * | 12/2012 | Ling | .................... | A61K 31/047 |
| | | | | 424/479 |

FOREIGN PATENT DOCUMENTS

| | | |
|---|---|---|
| CN | 103505599 A | 1/2014 |
| CN | 105327069 A | 2/2016 |

OTHER PUBLICATIONS

Fratkin, J.P., "Treating Infertility and Frequent Miscarriage with Chinese Herbal Medicine," https://drjakefratkin.com/articles/health-and-disease-articles/treating-infertility-and-frequent-miscarriage-with-chinese-herbal-medicine/infertility/, pp. 1-4. (Year: 2013).*
Yang, et al., J. Trad. and Comp. Med. 4:17 (Year: 2014).*
International Search Report for PCT/CN2017/071953, dated Mar. 15, 2015, ISA/CN.
Zhu Huawei, et al., Evaluation of curative effect of Shugan herbal products intervention brest pain, Journal of Practical Gynecologic Endocrinology, May 31, 2016, vol. 3, No. 5, pp. 7-8.
Liu Shuo, et al., Experimental Study on Antidepressant Effect of Shugan Jieyu 疏肝解郁 Plant Extracts, Chinese Journal of Traditional Medical Science and Technology, Jul. 31, 2016 vol. 23, No. 4, pp. 410-412.
Yang, Qiying, 80 Hyperplasia of mammary glands cases treated with Combined traditional Chinese and western medicine, Journal of Traditional Chinese Medicine of Shandong, Sep. 30, 1994, vol. 13 No. 9, p. 412.
Gao Yutong et al., Time dependent inhibitory effect of GTC on the breast ductal hyperplasia of rat induced by DMBA, Journal of Tianjin Medical University, Dec. 31, 2004, vol. 10, No. 4, pp. 500-509.

* cited by examiner

*Primary Examiner* — Michael Barker
(74) *Attorney, Agent, or Firm* — Yue (Robert) Xu; Apex Attorneys at Law, LLP (57) ABSTRACT

The present invention belongs to the field of Chinese herbal medicine products, and more particularly relates to a formulation, preparation method and use of a Chinese herbal medicine composition for soothing the liver. The present invention provides a Chinese herbal medicine composition for soothing the liver, wherein the raw materials of the composition comprise *Rhizoma Cyperi, Radix Angelicae Sinensis, Rhizoma Ligustici Chuanxiong, Radix Paeoniae Alba,* and *Pericarpium Citri Reticulatae.* The present invention further provides a preparation method of the composition, comprising: step 1, extracting; step 2, concentrating; and Step 3, drying. Moreover, the present invention provides the use of the composition and the product obtained by the method in the treatment of a breast disease and/or remission of depression.

3 Claims, 2 Drawing Sheets

FORMULATION, PREPARATION METHOD AND USE OF CHINESE HERBAL MEDICINE COMPOSITION FOR SOOTHING LIVER

CROSS REFERENCE TO RELATED APPLICATIONS

The present application is a National Phase entry of PCT Application No. PCT/CN2017/071953, filed on Jan. 20, 2017, which claims the priority of Chinese Patent Application No. 201510938258.0, as filed on Dec. 15, 2015 and titled with "FORMULATION, PREPARATION METHOD AND USE OF CHINESE HERBAL MEDICINE COMPOSITION FOR SOOTHING THE LIVER", and the disclosure of which is incorporated herein by reference.

FIELD

The present invention relates to the field of Chinese medicine products, and particularly relates to a formulation, a preparation method and an application of a Chinese herbal medicine composition for soothing the liver.

BACKGROUND

Liver controlling dispersion refers to the core physiological function of the liver, and dispersion per se means dredging releasing and venting, so as to obtain a certain satisfaction and pleasure of the body and mood. In particular, for female, Chinese medicine theory believes that the liver and breast are physiologically closely related. "Jueyin liver channel of foot extends up and passes through the diaphragm, distributes in the chest and hypochondrium and advances around the nipple", "female nipple belongs to liver". Liver stores blood, controls dispersion, and can directly adjust the profit and loss of Xuehai in Chong and Ren channels. If worry or angry, liver Qi will be stagnated and cannot be released, Qi and blood in Chong and Ren channels cannot flow, leading to Qi stagnation and blood stasis. Before menstruation, Qi and blood gather in Chong and Ren channels and block the meridians, exacerbating breast pain and increasing the lump; and after meridians, Xuehai is emptied and the breast pain is alleviated slightly, however, since the blood vessel is blocked and cannot be smoothed for long time, the breast clumps cannot be dissipated.

Western medicine believes that breast hyperplasia and other breast diseases are mainly associated with the imbalance of ovarian endocrine. Some researchers have found that patients with periodic breast pain show elevated estrogen level, reduced progesterone level, or imbalance between estrogen and progesterone, resulting in excessive breast hyperplasia or subinvolution and as a result, fibrosis, and breast pain. In the field of Western medicine, conventional Western medicine products for the treatment of breast hyperplasia are hormones, such as male hormones, progesterone and estrogen. However, hormone therapy has some disadvantages, such as large side effects, easy to relapse, easy to cause endocrine disorders and unsuitable for routine application.

In view of this, Chinese medicine means which treat breast hyperplasia and other breast diseases from the pathogenesis overcome the disadvantages of the hormone therapy, and have received more and more attention and research. Chinese medicine believed that breast hyperplasia and other breast diseases are caused by Qi stagnation, phlegm stasis, and blood stasis, which are gathered in the breast and cannot be dissipated for long time, due to emotional upset, stagnation of liver Qi, deficiency of vial Qi, and stagnant movement of Qi-blood circulation. Therefore, Chinese medicine treats these diseases mainly by relieving Qi stagnation in Liver, adjusting Chong and Ren channels and activating blood circulation to dissipate blood stasis. At the same time, Chinese medicine treats diseases according to syndrome differentiation in the overall concept, combining the disease differentiation with syndrome differentiation, overall treatment with local treatment, internal treatment with external treatment, long-term treatment with short-term treatment, so an to treat both root causes and symptoms. There are many medicaments on the market for the treatment of breast hyperplasia and other breast diseases, but these medicaments have some disadvantages, such as too many herbs, complicated preparation process, large administration dose, unsuitable for long-term use and poor consumer compliance.

Modern medicine believes that the pathological changes of depression are mainly related to the central nervous system, immune and neuroendocrine functions, although the exact pathogenesis is still not clear. At present, there are some arguments, such as mono-amine hypothesis, neurotransmitter receptor hypothesis, neuroendocrine function change hypothesis and immune system abnormalities hypothesis and so on. At present, clinically commonly used antidepressants include tricyclic, tetracyclic, neurotransmitter inhibitors and monoamine oxidase inhibitors and other drugs. However, such antidepressant Western medicine products have some disadvantages, such as large side effects, unsatisfactory efficacy, poor compliance, and expensive price, which restrict the clinical application.

In view of this, Chinese medicine means which treat depression from the pathogenesis overcome the disadvantages of the above Western medicine for treating depression, and have advantages such as considerable efficacy, quick effect, be capable of improving the quality of life of patients, reducing recurrence rate, less side effects, good patient compliance and other obvious advantages compared with the Western medicine for treating depression, thus have wide range of development and application space and have received more and more attention and research. Depression is a typical disease caused by biological, psychological, social and other factors, and can lead to pathological response in multi-system and multi-level in the body. Therefore, drug therapies with single role and clear target unavoidably have some disadvantages, and generally manifest adverse reactions and recurrence. In contrast, Chinese medicine therapies acting on multi-level and multi-target have certain potential and advantages. In the remission of depression, the traditional Chinese medicine theory believes that depression belongs to the "yu zheng (melancholia)" category, and Qi activity disorder in Five Zang-organs is the basic pathogenesis of the disorder. In Five Zang-organs, liver has the closest relationship with melancholia, since liver controls dispersion and is the main reservoir of blood. Liver controlling dispersion means liver has the function of dredging, comforting, dispersing the qi activity in the body, so that it is smooth and no blocked, scattered and not stagnated. Liver controlling dispersion also has the role of emotional regulation. Liver controlling dispersion plays an important role in the balance and coordination of the rise and fall as well as entry and exit of Qi activity in all Zang-organs and Fu-organs in the body. So "Essay after Reading Medicine" describes "conversion of Qi of all the Twelve Regular Meridians in Zang-organs and Fu-organs must be boosted by the conversion of Qi of liver and gallbladder, so as to be smooth and not sick". Therefore, if the function of liver controlling dispersion is normal, then the movement of Qi is in a harmonious way, Qi and blood are harmonious, meridians are smooth, and the activities of Zang-organs and Fu-organs can be properly adjusted. In normal physiological circumstances, the liver controlling dispersion is normal, and liver Qi rise, neither excitement, nor depression, but is comfortable and orderly, then people will be able to better coordinate their mental activity, reflected as happy spirit, comfortable feeling, sensible and bright, sensitive thinking, smooth Qi leading to harmony emotions, and harmony of Qi and Blood. If liver controlling dispersion is not normal, Qi activity will be stagnated, followed by a series of clinical manifestations of depression. However, the ease of depression using traditional Chinese medicine products is only a theoretical deduction and research, and there is no mature Chinese medicine prescription for the relief of depression.

In summary, the existing Chinese medicine prescription products for breast diseases such as breast hyperplasia and the like have disadvantages, such as too many herbs, complicated preparation process, large administration dose, unsuitable for long-term use and poor consumer compliance, and there is a lack of Chinese medicine products for relieving depression. Therefore, there is an urgent need to develop a Chinese herbal medicine composition and the preparation method thereof, which has the advantages of simple formulation, simple preparation process, small dosage, suitable for long-term use and good consumer compliance, and can treat breast diseases such as breast hyperplasia and alleviate depression at the same time.

SUMMARY

In view of the above, the present invention provides a formulation, a preparation method and a use of a Chinese herbal medicine composition for soothing the liver, to overcome the disadvantages, for example, too many herbs, complicated preparation process, large administration dose, unsuitable for long-term use and poor consumer compliance, of the existing Chinese medicine prescription product for breast diseases such as breast hyperplasia and the like, as well as the lack of Chinese medicine products for relieving depression.

The present invention provides a Chinese herbal medicine composition for soothing the liver, wherein the raw materials of the composition comprise *Rhizoma Cyperi, Radix Angelicae Sinensis, Rhizoma Ligustici Chuanxiong, Radix Paeoniae Alba,* and *Pericarpium Citri Reticulatae.*

Preferably, the raw materials of the composition further comprise a green tea extract.

Preferably, the raw materials of the composition comprise: 20-50 parts by weight of *Rhizoma Cyperi,* 10-30 parts by weight of *Radix Angelicae Sinensis,* 10-30 parts by weight of *Rhizoma Ligustici Chuanxiong,* 5-20 parts by weight of *Radix Paeoniae Alba,* and 5-20 parts by weight of *Pericarpium Citri Reticulatae.*

Preferably, the raw materials of the composition further comprise 0.5-10 parts by weight of green tea extract.

Preferably, the content of tea polyphenol in the green tea extract is not less than 30%.

The present invention provides a preparing method for the Chinese herbal medicine composition for soothing the liver according to any one as mentioned above, wherein the method comprises: step 1, extracting: adding the first amount of a solvent to the mixture of *Rhizoma Cyperi, Radix Angelicae Sinensis, Rhizoma Ligustici Chuanxiong, Radix Paeoniae Alba,* and *Pericarpium Citri Reticulatae* to perform the first extraction, filtering and collecting the first filtrate; adding the second amount of the solvent to perform the second extraction, filtering and collecting the second filtrate; combining the first filtrate and the second filtrate to obtain the extract; step 2, concentrating; and step 3, drying.

Preferably, the solvent is selected from water, ethanol or other solvents.

Preferably, the preparing method further comprises: mixing the product obtained after drying with a green tea extract.

Preferably, the preparation method comprises mixing *Rhizoma Cyperi, Radix Angelicae Sinensis, Rhizoma Ligustici Chuanxiong, Radix Paeoniae Alba,* and *Pericarpium Citri Reticulatae* proportionally and preparing them into a powder, or mixing the powders of *Rhizoma Cyperi, Radix Angelicae Sinensis, Rhizoma Ligustici Chuanxiong, Radix Paeoniae Alba,* and *Pericarpium Citri Reticulatae* proportionally.

Preferably, the mixed powder is mixed with the green tea extract to obtain the product of the present invention.

Preferably, the mass ratio of the first amount of the solvent to the mixture is (9-12):1, the extraction time of the first extraction is 1 to 3 hours, and the extraction condition of the first extraction is in boiling; the mass ratio of the second amount of the solvent to the mixture is (7-10):1, the extraction time of the second extraction is 0.5 to 1.5 hours, and the extraction condition of the second extraction is in boiling; the concentrating process is concentrating the extract under reduced pressure to give a concentrated product; the solid content of the concentrated product is 20 to 30%.

Preferably, the solvent is selected from water, ethanol or other solvents.

Preferably, the preparing method further comprises: preparing the product obtained after drying into an oral preparation in a dosage form selected from one or more of oral liquid, powder, granule, tablet and capsule.

The present invention also provides use of the Chinese herbal medicine composition for soothing the liver according to any one as mentioned above, or the product prepared by the method according to any one as mentioned above in the treatment of a breast disease and/or remission of depression.

In sum, the present invention starts from the theoretical basis of Chinese medicine for a breast disease such as breast hyperplasia and depression, supplemented by the compatibility of Chinese medicine, finds a formulation and preparing method of a Chinese herbal medicine composition for soothing the liver, which overcomes the disadvantages, for example, too many herbs, complicated preparation process, large administration dose, unsuitable for long-term use and poor consumer compliance, of the existing Chinese medicine prescription product for breast diseases such as breast hyperplasia and the like, as well as the lack of Chinese medicine products for relieving depression. The invention initiates a Chinese medicine product which can simultaneously treat the breast disease and alleviate the depression, and has a milestone significance for the research and development of the Chinese medicine product.

BRIEF DESCRIPTION OF THE DRAWINGS

In order to more clearly illustrate the embodiments of the present invention or the technical solutions in the prior art, the following drawings, which are to be used in the description of the embodiments or the prior art, will be briefly described. It will be apparent that the drawings in the following description is embodiments of the present invention, and it will be apparent to those skilled in the art that other drawings may be obtained in accordance with the drawings provided without inventive work.

Here, FIG. 4 is designated as the drawing for the abstract.

DETAILED DESCRIPTION

The technical solutions in the examples of the present invention will now be described more clearly and completely, and it will be apparent that the described examples are merely part of the examples of the invention and are not intended to be exhaustive. All other examples obtained without creative work by those skilled in the art are within the scope of the present invention.

For a more detailed description of the present invention, the formulation, preparing method and use of the Chinese herbal medicine composition for soothing the liver will be provided and described in detail with reference to the following examples.

Example 1

30 g of *Rhizoma Cyperi*, 20 g of *Radix Angelicae Sinensis*, 20 g of *Rhizoma Ligustici Chuanxiong*, 10 g of *Radix Paeoniae Alba*, and 10 g of *Pericarpium Citri Reticulatae* were weighed to obtain a total of 90 g of mixture. After adding 0.9 Kg of water, the mixture was heated at 100° C. for 1.5 h. The filtrate was collected by filtration. After adding 0.72 Kg of water to the residue, the mixture was heated at 100° C. for 1 hour. The filtrate was collected by filtration. The two filtrates were combined. Using the conventional reduced pressure concentration method, the combined filtrate was concentrated to a solid content of 20%. A fine powder was obtained by the conventional spray drying. The obtained fine powder was mixed with 2 g of green tea extract (green tea extract purchased from Shaanxi Golden Harvest Botanical Chemical Co., Ltd., the green tea extract has a tea polyphenol content greater than or equal to 98%), to obtain product 1.

Example 2

50 g of *Rhizoma Cyperi*, 10 g of *Radix Angelicae Sinensis*, 10 g of *Rhizoma Ligustici Chuanxiong*, 20 g of *Radix Paeoniae Alba*, and 5 g of *Pericarpium Citri Reticulatae* were weighed to obtain a total of 95 g of mixture. After adding 0.95 Kg of water, the mixture was heated at 100° C. for 3 h. The filtrate was collected by filtration. After adding 0.665 Kg of water to the residue, the mixture was heated at 100° C. for 1.5 hour. The filtrate was collected by filtration. The two filtrates were combined. Using the conventional reduced pressure concentration method, the combined filtrate was concentrated to a solid content of 30%. A fine powder was obtained by the conventional spray drying. The obtained fine powder was mixed with 8 g of green tea extract (green tea extract purchased from Shaanxi Golden Harvest Botanical Chemical Co., Ltd., the green tea extract has a tea polyphenol content of 30%), to obtain product 2.

Example 3

20 g of *Rhizoma Cyperi*, 30 g of *Radix Angelicae Sinensis*, 30 g of *Rhizoma Ligustici Chuanxiong*, 5 g of *Radix Paeoniae Alba*, and 20 g of *Pericarpium Citri Reticulatae* were weighed to obtain a total of 105 g of mixture. After adding 1 Kg of water, the mixture was heated at 100° C. for 1 h. The filtrate was collected by filtration. After adding 1.05 Kg of water to the residue, the mixture was heated at 100° C. for 1 hour. The filtrate was collected by filtration. The two filtrates were combined. The combined filtrate was concentrated to a solid content of 20%. A fine powder was obtained by the conventional spray drying. The obtained fine powder was mixed with 0.5 g of green tea extract (green tea extract purchased from Shaanxi Golden Harvest Botanical Chemical Co., Ltd., the green tea extract has a tea polyphenol content of 60%), to obtain product 3.

Example 4

35 g of *Rhizoma Cyperi*, 15 g of *Radix Angelicae Sinensis*, 15 g of *Rhizoma Ligustici Chuanxiong*, 15 g of *Radix Paeoniae Alba*, and 10 g of *Pericarpium Citri Reticulatae* were weighed to obtain a total of 90 g of mixture. After adding 0.9 Kg of water, the mixture was heated at 100° C. for 1 h. The filtrate was collected by filtration. After adding 0.72 Kg of water to the residue, the mixture was heated at 100° C. for 1 hour. The filtrate was collected by filtration. The two filtrates were combined. Using the conventional reduced pressure concentration method, the combined filtrate was concentrated to a solid content of 30%. A fine powder was obtained by the conventional spray drying. The obtained fine powder was mixed with 1 g of green tea extract (green tea extract purchased from Shaanxi Golden Harvest Botanical Chemical Co., Ltd., the green tea extract has a tea polyphenol content of 90%), to obtain product 4.

Example 5

25 g of *Rhizoma Cyperi*, 25 g of *Radix Angelicae Sinensis*, 25 g of *Rhizoma Ligustici Chuanxiong*, 10 g of *Radix Paeoniae Alba*, and 15 g of *Pericarpium Citri Reticulatae* were weighed to obtain a total of 100 g of mixture. After adding 1.2 Kg of water, the mixture was heated at 100° C. for 3 h. The filtrate was collected by filtration. After adding 1 Kg of water to the residue, the mixture was heated at 100° C. for 1.5 hour. The filtrate was collected by filtration. The two filtrates were combined. The combined filtrate was concentrated to a solid content of 20%. A fine powder was obtained by the conventional spray drying. The obtained fine powder was mixed with 2 g of green tea extract (green tea extract purchased from Shaanxi Golden Harvest Botanical Chemical Co., Ltd., the green tea extract has a tea polyphenol content of 98%), to obtain product 5.

Example 6

30 g of *Rhizoma Cyperi*, 20 g of *Radix Angelicae Sinensis*, 20 g of *Rhizoma Ligustici Chuanxiong*, 10 g of *Radix Paeoniae Alba*, and 10 g of *Pericarpium Citri Reticulatae* were weighed to obtain a total of 90 g of mixture. After adding 0.9 Kg of water, the mixture was heated at 100° C. for 1.5 h. The filtrate was collected by filtration. After adding 0.72 Kg of water to the residue, the mixture was heated at 100° C. for 1 hour. The filtrate was collected by filtration. The two filtrates were combined. Using the conventional reduced pressure concentration method, the combined filtrate was concentrated to a solid content of 20%. A fine powder was obtained by the conventional spray drying, to obtain product 6.

Example 7

50 g of *Rhizoma Cyperi*, 10 g of *Radix Angelicae Sinensis*, 10 g of *Rhizoma Ligustici Chuanxiong*, 20 g of *Radix Paeoniae Alba*, and 5 g of *Pericarpium Citri Reticulatae* were weighed to obtain a total of 95 g of mixture. After adding 0.95 Kg of water, the mixture was heated at 100° C. for 3 h. The filtrate was collected by filtration. After adding 0.665 Kg of water to the residue, the mixture was heated at 100° C. for 1.5 hour. The filtrate was collected by filtration. The two filtrates were combined. Using the conventional reduced pressure concentration method, the combined filtrate was concentrated to a solid content of 30%. A fine powder was obtained by the conventional spray drying, to obtain product 7.

Example 8

20 g of *Rhizoma Cyperi*, 30 g of *Radix Angelicae Sinensis*, 30 g of *Rhizoma Ligustici Chuanxiong*, 5 g of *Radix Paeoniae Alba*, and 20 g of *Pericarpium Citri Reticulatae* were weighed to obtain a total of 105 g of mixture. After adding 1 Kg of water, the mixture was heated at 100° C. for 1 h. The filtrate was collected by filtration. After adding 1.05 Kg of water to the residue, the mixture was heated at 100° C. for 1 hour. The filtrate was collected by filtration. The two filtrates were combined. The combined filtrate was concentrated to a solid content of 20%. A fine powder was obtained by the conventional spray drying, to obtain product 8.

Example 9

35 g of *Rhizoma Cyperi*, 15 g of *Radix Angelicae Sinensis*, 15 g of *Rhizoma Ligustici Chuanxiong*, 15 g of *Radix Paeoniae Alba*, 10 g of *Pericarpium Citri Reticulatae* and 5 g green tea were weighed, mixed and prepared into a uniform powder, to obtain product 9.

Example 10

25 g of *Rhizoma Cyperi*, 25 g of *Radix Angelicae Sinensis*, 25 g of *Rhizoma Ligustici Chuanxiong*, 10 g of *Radix Paeoniae Alba*, and 15 g of *Pericarpium Citri Reticulatae* were weighed to obtain a total of 100 g of mixture. After adding 1.2 Kg of ethanol, the mixture was heated under boiling reflux for 3 h. The filtrate was collected by filtration. After adding 1 Kg of ethanol to the residue, the mixture was heated under boiling reflux for 1.5 hour. The filtrate was collected by filtration. The two filtrates were combined. The combined filtrate was concentrated to a solid content of 20%. A fine powder was obtained by the conventional spray drying, to obtain product 10.

Example 11

The product 1 obtained in Example 1 was prepared into any one of oral liquid, powder, granule, tablet and capsule, respectively, according to a conventional formulation method.

Similarly, the products in Examples 2 to 10 were prepared into any one of oral liquid, powder, granule, tablet and capsule, respectively, according to a conventional formulation method.

Example 12

This example provides an experimental study of product 1 for the treatment of breast hyperplasia in animals
1. Experimental Material
1.1 Test Product
Product 1 obtained from Example 1, with an appearance of brownish yellow powder, and a unique aroma of this product.
1.2 Positive Control
Rupixiao Table, purchased from Liaoning Good Nurses Pharmaceutical (Group) Co., Ltd., batch number 121122, oral administration, with a dose of 6 tables per time, 3 times a day, with a weight of 0.32 g/tablet.
1.3 Reagents and Medicines
Estradiol benzoate injection, progesterone injection, rat estradiol enzyme-linked immunosorbent assay kit, rat prolactin enzyme-linked immunosorbent assay kit, rat progesterone enzyme-linked immunosorbent assay kit, rat follicle-stimulating hormone enzyme-linked immunosorbent assay kit, rat luteinizing hormone enzyme-linked immunosorbent assay kit, and 0.9% sodium chloride injection.
2 Experimental Method
2.1 Animal Grouping
Sixty SPF grade SD female rats were randomly divided into 6 groups (n=10): normal control group, model control group, product 1 high, medium and low dose groups and Rupixiao group.
2.2 Dose Setting
Product 1 high dose group: 752.32 mg·kg$^{-1}$/day, prepared by grinding after adding distilled water;
Product 1 medium dose group: 376.16 mg·kg$^{-1}$/day, prepared by grinding after adding distilled water;
Product 1 low dose group: 188.08 mg·kg$^{-1}$/day, prepared by grinding after adding distilled water;
Rupixiao group: 960.00 mg·kg$^{-1}$/day, prepared by grinding according to dose after adding distilled water in the experiments.
2.3 Experimental Statistical Methods
All measurement data are expressed as mean±standard deviation ($\bar{x}\pm s$). The comparison of mean among multiple groups was performed based on one-way ANOVA, and the comparison of mean between groups was performed with pairwise comparison, using SNK method for homoscedasticity, and using Dunnett's T3 method for heteroscedasticity. Data statistics was performed by SPSS15.0 software.
2.4 Methods of Administration
Animals in product 1 high, medium and low dose groups and Rupixiao group were intragastrically administered with the drug according the dose, with an administration volume of 10 ml·kg$^{-1}$, once a day for 30 days. Animals in the normal control group and the model control group were intragastrically administered with distilled water in an administration volume of 10 ml·kg$^{-1}$ in the same way.
2.5 Test Method
Except for the normal control group, rats in other five groups were intramuscularly injected with estradiol benzoate at 0.5 mg·kg$^{-1}$, once a day for 25 days. Subsequently, these animals were intramuscularly injected with progesterone at 4 mg·kg$^{-1}$, once a day for 5 days. Animals in the normal control group were not intramuscularly injected with hormones, instead with saline at 0.2 ml/animal for 30 days.

At the same time, animals in product 2 high, medium and low dose groups and Rupixiao group were intragastrically administered with the drug, and animals in the normal control group and the model control group were intragastrically administered with distilled water, once a day for 30 days.

After 1 h of the last administration, the diameter and height of the second pair of nipples were measured with a vernier caliper and the appearance was observed. Blood samples were collected from animal orbital venous plexus and serum was isolated for measuring the serum content of estradiol E2, progesterone P, prolactin PRL, luteinizing hormone LH and follicle-stimulating hormone FSH in the animals. After the local hair removal treatment with 8% sodium sulfide, the animals were sacrificed and the second pair of breasts in the rat chest were completely peeled off and removed. After fixed with 10% formaldehyde solution, embedded in paraffin, and stained with hematoxylin-eosin (HE), the tissue of the second pair of breast were observed under an optical microscope.

3 Experimental Results 3.1 Effect on the Diameter and Height of the Second Pair of Nipples in Breast Hyperplasia Rats Compared with the normal control group, the diameter and height of the second pair of nipples were increased significantly in the model control group ($P<0.01$). Compared with the model control group, the diameter and height of the second pair of nipples were significantly reduced in product 2 high, medium and low dose groups and Rupixiao group ($P<0.01$). See Table 1 for specific experimental results.

TABLE 1

Effects on the diameter and height of the second pair of nipples in breast hyperplasia rats ($\bar{x} \pm s$, n = 10)

| Group | dose | nipple diameter (mm) | nipple height (mm) |
|---|---|---|---|
| Normal control group | — | 2.005 ± 0.084 | 1.726 ± 0.074 |
| Model control group | — | 2.712 ± 0.092** | 2.608 ± 0.078** |
| Pro. 1 high dose group | 752.32 mg · kg$^{-1}$ | 2.227 ± 0.070## | 2.044 ± 0.131## |
| Pro. 1 medium dose group | 376.16 mg · kg$^{-1}$ | 2.347 ± 0.090## | 2.088 ± 0.087## |
| Pro. 1 low dose group | 188.08 mg · kg$^{-1}$ | 2.338 ± 0.081## | 2.178 ± 0.131## |
| Rupixiao group | 960.00 mg · kg$^{-1}$ | 2.385 ± 0.100## | 2.298 ± 0.067## |

Note:
*$P < 0.05$,
**$P < 0.01$ vs. the normal control group;
$P < 0.05$,
$P < 0.01$ vs. the model control group.

3.2 Effects on Serum Estradiol E2 and Progesterone P Content in Breast Hyperplasia Rats Compared with the normal control group, the content of estradiol E2 and progesterone P were significantly increased in the model control group ($P<0.01$). Compared with the model control group, the content of estradiol E2 and progesterone P were significantly decreased in the Chinese herbal compound high, medium and low dose groups and Rupixiao group ($P<0.01$ or $P<0.05$). See Table 2 for specific experimental results.

TABLE 2

Effects on serum estradiol E2 and progesterone P content in breast hyperplasia rats ($\bar{x} \pm s$, n = 10)

| Group | dose | estradiol E2 (pg/ml) | progesterone P (pg/ml) |
|---|---|---|---|
| Normal control group | — | 57.561 ± 12.266 | 80.612 ± 27.006 |
| Model control group | — | 519.575 ± 95.894** | 192.402 ± 24.656** |
| Pro. 1 high dose group | 752.32 mg · kg$^{-1}$ | 292.527 ± 45.608## | 115.348 ± 18.061## |
| Pro. 1 medium dose group | 376.16 mg · kg$^{-1}$ | 379.909 ± 90.746## | 118.909 ± 24.879## |
| Pro. 1 low dose group | 188.08 mg · kg$^{-1}$ | 384.118 ± 109.562## | 146.971 ± 29.330## |
| Rupixiao group | 960.00 mg · kg$^{-1}$ | 430.787 ± 92.299# | 133.174 ± 28.961## |

Note:
*$P < 0.05$,
**$P < 0.01$ vs. the normal control group;
$P < 0.05$,
$P < 0.01$ vs. the model control group.

3.3 Effects on Serum Prolactin PRL, Luteinizing Hormone LH and Follicle-Stimulating Hormone FSH Content in Breast Hyperplasia Rats Compared with the normal control group, the contents of prolactin PRL, luteinizing hormone LH and follicle-stimulating hormone FSH were significantly increased in the model control group (P<0.01). Compared with the model control group, the contents of prolactin PRL, luteinizing hormone LH and follicle stimulating hormone FSH were significantly decreased in product 1 high, medium and low dose groups and Rupixiao group (P<0.01). See Table 3 for specific experimental results.

TABLE 3

Effect on serum PRL, LH, FSH content in breast hyperplasia rats ($\bar{x} \pm s$, n = 10)

| group | dose (mg·kg$^{-1}$) | Prolactin PRL (pg/ml) | luteinizing hormone LH (pg/ml) | follicle stimulating hormone FSH (pg/ml) |
|---|---|---|---|---|
| Normal control group | — | 1.223 ± 0.189 | 1.726 ± 0.494 | 3.524 ± 0.934 |
| Model control group | — | 4.593 ± 0.879** | 3.526 ± 0.558** | 15.616 ± 2.908** |
| Pro. 1 high dose group | 752.32 | 2.042 ± 0.707## | 2.291 ± 0.404## | 10.219 ± 2.639## |
| Pro. 1 medium dose group | 376.16 | 2.136 ± 0.857## | 2.223 ± 0.357## | 11.165 ± 3.173## |
| Pro. 1 low dose group | 188.08 | 2.742 ± 0.671## | 2.781 ± 0.292## | 11.818 ± 2.013## |
| Rupixiao group | 960.00 | 2.848 ± 0.781## | 2.834 ± 0.490## | 11.210 ± 2.513## |

Note:
*P < 0.05,
**P < 0.01 vs. the normal control group;
P < 0.05,
P < 0.01 vs. the model control group.

3.4 Observation of the Pathological Morphology of the Second Pair of Nipples in Breast Hyperplasia Rats General observation. In the control group, the shapes of the nipples were the same as at the beginning of the experiments. The position of the nipples cannot be seen across the hair, and after the hair was separated, only millet-like nipples can be found, which were closely affixed to the skin, pale and soft, with individual nipples slightly uplifted (about 1 mm). In the model control group, the morphological changes of the nipples were erect, more solid, congested, and increased height (2 to 3 mm). In the treatment group, the nipples of the rats were erected and had significantly reduced congestion.

Figure 1:
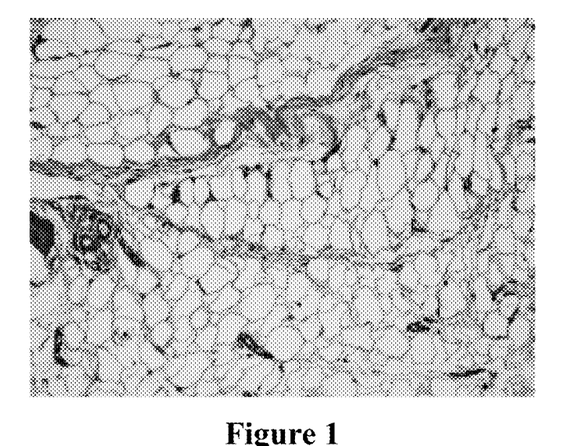
FIG. 1 is a photomicrograph of a breast slice of the normal control group according to Example 8 of the present invention.
Figure 2:
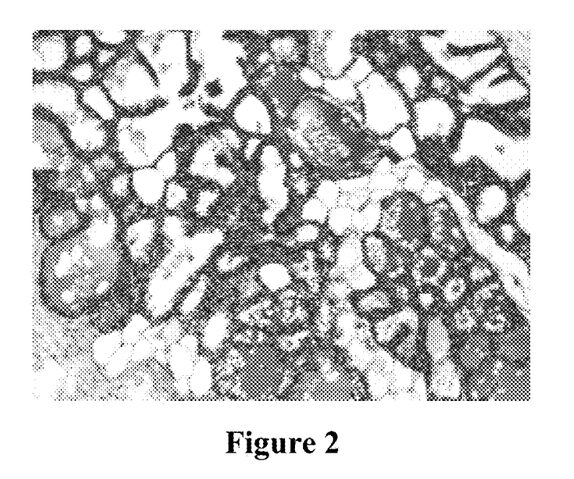
FIG. 2 is a photomicrograph of a breast slice of the model control group according to Example 8 of the present invention.
Figure 3:
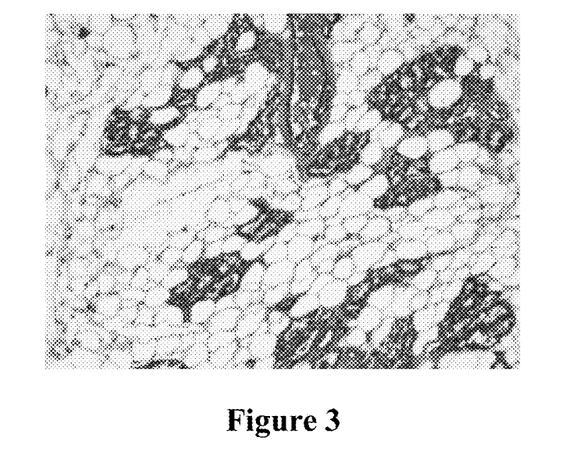
FIG. 3 is a photograph of a breast slice of the Rupixiao group according to Example 8 of the present invention.
Figure 4:
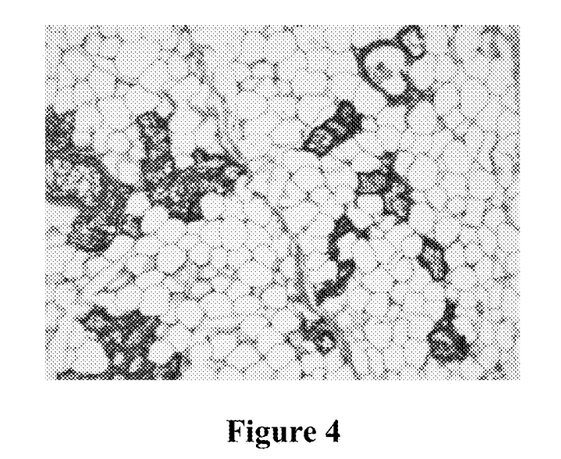
FIG. 4 is a photograph of a breast slice of the claimed product according to Example 8 of the present invention.

Microscopic observation. In the normal control group, there was no significant proliferation in the breast lobule and acini, in which the number of acini was 4 to 5, and no acini cavity was enlarged. In the model control group, the number of breast lobules and acini increased significantly, some acini cavitys were enlarged and had secretions inside; some breast ductal epithelial cells proliferate significantly, with local papillary or stratified hyperplasia, the duct cavity were enlarged and had exfoliated epithelial cells and their secretions inside, accompanied by interstitial fibrous tissue hyperplasia. In the treatment group, the number of breast lobules and acini were significantly reduced, and the proliferation of breast ductal epithelial cells was significantly reduced.

As shown from Example 4, product 1 obtained in Example 1 is a good medicament for the treatment of breast hyperplasia. The high, medium and low doses of Example 1 had a significant inhibitory effect on rat breast hyperplasia. The therapeutic effect of the low-dose group of Example 1 on breast hyperplasia was comparable to that of the commercially available Rupihide tablets, but the dose was only ⅕ of that of the nipple Rupihide tablets, thus is significantly reduced.

The above experiments were repeated using the products obtained in Examples 2 to 10, and similar experimental results were obtained, and the description thereof will not be repeated here.

Example 13

This example provides an experimental study of product 6 for the treatment of breast hyperplasia in animals 1. Experimental Material
1.1 Test Product Product 6 obtained from Example 6, with an appearance of brownish yellow powder, and a unique aroma of this product.

1.2 Positive Control

Rupixiao Tablet, purchased from Liaoning good nurses Pharmaceutical (Group) Co., Ltd., batch number 121122, oral administration, with a dose of 6 tablets per time, 3 times a day, with a weight of 0.32 g/tablet.

1.3 Reagents and Medicines

Estradiol benzoate injection, progesterone injection, rat estradiol enzyme-linked immunosorbent assay kit, rat prolactin enzyme-linked immunosorbent assay kit, rat progesterone enzyme-linked immunosorbent assay kit, rat follicle-stimulating hormone enzyme-linked immunosorbent assay kit, rat luteinizing hormone enzyme-linked immunosorbent assay kit, and 0.9% sodium chloride injection.

2 Experimental Method
2.1 Animal Grouping

Forty SPF grade SD female rats were randomly divided into 4 groups (n=10): normal control group, model control group, product 6 group and Rupixiao group.

2.2 Dose Setting

Product 6 group: 342.83 mg·kg$^{-1}$/day, prepared by grinding according to dose after adding distilled water in the experiments;

Rupixiao group: 960.00 mg·kg$^{-1}$/day, prepared by grinding according to dose after adding distilled water in the experiments.

2.3 Experimental Statistical Methods

All measurement data are expressed as mean±standard deviation ($\bar{x}\pm s$). The comparison of mean among multiple groups was performed based on one-way ANOVA, and the comparison of mean between groups was performed with pairwise comparison, using SNK method for homoscedasticity, and using Dunnett's T3 method for heteroscedasticity. Data statistics was performed by SPSS15.0 software.

2.4 Methods of Administration

Animals in product 6 group and Rupixiao group were intragastrically administered with the drug according the dose, with an administration volume of 10 ml·kg$^{-1}$, once a day for 30 days. Animals in the normal control group and the model control group were intragastrically administered with distilled water in an administration volume of 10 ml·kg$^{-1}$ in the same way.

2.5 Test Method

Except for the normal control group, rats in other three groups were intramuscularly injected with estradiol benzoate at 0.5 mg·kg$^{-1}$, once a day for 25 days. Subsequently, these animals were intramuscularly injected with progesterone at 4 mg·kg$^{-1}$, once a day for 5 days. Animals in the normal control group were not intramuscularly injected with hormones, instead with saline at 0.2 ml/animal for 30 days. At the same time, animals in product 6 group and Rupixiao group were intragastrically administered with the drug, and animals in the normal control group and the model control group were intragastrically administered with distilled water, once a day for 30 days.

After 1 h of the last administration, the diameter and height of the second pair of nipples were measured with a vernier caliper and the appearance was observed. Blood samples were collected from animal orbital venous plexus and serum was isolated for measuring the serum content of estradiol E2, progesterone P, prolactin PRL, luteinizing hormone LH and follicle-stimulating hormone FSH in the animals. After the local hair removal treatment with 8% sodium sulfide, the animals were sacrificed and the second pair of breasts in the rat chest were completely peeled off and removed. After fixed with 10% formaldehyde solution, embedded in paraffin, and stained with hematoxylin-eosin (HE), the tissue of the second pair of breast were observed under an optical microscope.

3 Experimental Results 3.1 Effect on the Diameter and Height of the Second Pair of Nipples in Breast Hyperplasia Rats As shown in table 4, compared with the normal control group, the diameter and height of the second pair of nipples were increased significantly in the model control group (P<0.01). Compared with the model control group, the diameter and height of the second pair of nipples were increased reduced in product 6 group and Rupixiao group (P<0.01).

TABLE 4

Effects on the diameter and height of the second pair of nipples in breast hyperplasia rats ($\bar{x} \pm s$, n = 10)

| Group | dose | nipple diameter (mm) | nipple height (mm) |
|---|---|---|---|
| Normal control group | — | 1.891 ± 0.111 | 1.611 ± 0.095 |
| Model control group | — | 2.597 ± 0.107** | 2.458 ± 0.078** |
| Pro. 6 group | 342.83 mg·kg−1 | 2.190 ± 0.127## | 2.038 ± 0.087## |
| Rupixiao group | 960.00 mg·kg−1 | 2.278 ± 0.099## | 2.143 ± 0.106## |

Note:
*P < 0.05,
**P < 0.01 vs. the normal control group;
P < 0.05,
P < 0.01 vs. the model control group.

3.2 Effects on Serum Estradiol E2 and Progesterone P Content in Breast Hyperplasia Rats As shown in table 4, Compared with the normal control group, the content of estradiol E2 and progesterone P were significantly increased in the model control group (P<0.01). Compared with the model control group, the content of estradiol E2 was significantly decreased in product 6 group and Rupixiao group (P<0.01), and the content of progesterone P was significantly decreased in product 6 group and Rupixiao group (P<0.01 or P<0.05).

TABLE 5

Effects of serum estradiol E2 and progesterone P content in breast hyperplasia rats ($\bar{x} \pm s$, n = 10)

| Group | dose | estradiol E2 (pg/ml) | progesterone P (pg/ml) |
|---|---|---|---|
| Normal control group | — | 55.464 ± 18.212 | 64.920 ± 21.749 |
| Model control group | — | 492.953 ± 75.555** | 225.209 ± 28.860** |
| Pro. 6 group | 342.83 mg·kg−1 | 391.107 ± 80.681## | 173.664 ± 43.075# |
| Rupixiao group | 960.00 mg·kg−1 | 319.583 ± 77.398## | 182.919 ± 33.989# |

Note:
*P < 0.05,
**P < 0.01 vs. the normal control group;
P < 0.05,
P < 0.01 vs. the model control group.

3.3 Effects on Serum Prolactin PRL, Luteinizing Hormone LH and Follicle-Stimulating Hormone FSH Content in Breast Hyperplasia Rats As shown in table 6, Compared with the normal control group, the contents of prolactin PRL, luteinizing hormone LH and follicle-stimulating hormone SH were significantly increased in the model control group (P<0.01). Compared with the model control group, the contents of prolactin PRL, luteinizing hormone LH and follicle stimulating hormone FSH were significantly decreased in product 6 group and Rupixiao group (P<0.01 or P<0.05).

TABLE 6

Effect on serum PRL, LH, FSH content in breast hyperplasia rats
($\bar{x} \pm s$, n = 10)

| group | dose | Prolactin PRL (pg/ml) | luteinizing hormone LH (pg/ml) | follicle stimulating hormone FSH (pg/ml) |
|---|---|---|---|---|
| Normal control group | — | 1.214 ± 0.183 | 2.102 ± 0.517 | 6.520 ± 1.533 |
| Model control group | — | 8.270 ± 1.583** | 3.813 ± 0.800** | 19.136 ± 3.343** |
| Pro. 6 group | 342.83 mg · kg−1 | 4.176 ± 2.216## | 2.825 ± 0.567## | 14.465 ± 3.305# |
| Rupixiao group | 960.00 mg · kg−1 | 4.205 ± 1.937## | 2.760 ± 0.592# | 14.039 ± 5.002# |

Note:
*$P < 0.05$,
**$P < 0.01$ vs. the normal control group;
$P < 0.05$,
$P < 0.01$ vs. the model control group.

3.4 Observation on Pathological Morphology of the Second Pair of Nipples in Breast Hyperplasia Rats General Observation.

In the normal control group, the shapes of the nipples were the same as at the beginning of the experiments. The position of the nipples cannot be seen across the hair, and after the hair was separated, only millet-like nipples can be found, which were closely affixed to the skin, pale and soft, with individual nipples slightly uplifted (about 1 mm). In the model control group, the morphological changes of the nipples were erect, more solid, congested, and increased height (2 to 3 mm). In the treatment group, the nipples of the rats were erected and had significantly reduced congestion.

Microscopic Observation.

In the normal control group, there was no significant proliferation in the breast lobule and acini, in which the number of acini was 4 to 5, and no acini cavity was enlarged. In the model control group, the number of breast lobules and acini increased significantly, some acini cavitys were enlarged and had secretions inside; some breast ductal epithelial cells proliferate significantly, with local papillary or stratified hyperplasia, the duct cavity were enlarged and had exfoliated epithelial cells and their secretions inside, accompanied by interstitial fibrous tissue hyperplasia. In product 6 group, the number of breast lobules and acini were significantly reduced, and the proliferation of breast ductal epithelial cells was significantly reduced.

The above experiments were repeated using the products obtained in Examples 1-5 and 7-10, and similar experimental results were obtained, and the description thereof will not be repeated here.

Example 14

This example provides an experimental study of product 1 for the improvement of condition in volunteers of clinical breast patients.

Recruitment object: performed according to "Guiding Principles of Clinical Research on new Chinese medicine", "Surgery of Chinese Medicine" (sixth edition). The volunteers recruited in this example had the clinical manifestations of breast pain and breast lumps, and under breast color ultrasound, the glandular tissue of the breast shown echo disorder or less uniform echo enhancement, the catheters showed visible cystic dilatation, thus they were clinically diagnosed as breast hyperplasia. Combined with product characteristics, the breast color ultrasound was introduced as grouping criteria: breast pain group-no obvious abnormality of breast was found; breast hyperplasia group-nodules or cysts <1 CM was found under color ultrasound.

The volunteers recruited in this example were female, ages 25-50, with essentially regular menstrual cycle and menstrual period of (28±7) days. The subjects had visual simulation score 0<(VAS)>7, and mild pain, or moderate pain when grouped. The subjects had periodic premenstrual breast pain symptom history, and B ultrasound and hand diagnosis results shown breast pain and mild breast hyperplasia. The subjects did not receive breast disease treatment within 1 month, and did not use hormone preparations within six months.

Through the recruitment, a total of 165 cases were obtained for clinical trials, including 52 cases of breast pain, and 113 cases of breast hyperplasia.

From the overall situation, after administrated with the product for 3 months, a total effectiveness of 68.9% was achieved, and in terms of improvement degree, the recovered subjects accounted for 32.9% of the total samples, with markedly effective of 5.5%, and effective of 30.5%. According to the comprehensive evaluation of clinical efficacy, the product of the invention had obvious curative effect on breast pain and breast hyperplasia, and no patient showed significant side effects during the administration, confirming that the product of the invention is a safe and effective drug for the treatment of breast hyperplasia.

The above experiments were repeated using the products obtained in Examples 2 to 10, and similar experimental results were obtained, and the description thereof will not be repeated here.

Example 15

This example provides an experimental study of product 1 for improving depression in depression animals.

1 Experimental Animals and Grouping

The experimental animals were SD rats weighing 200±10 g, provided by Animal Experimental Center of Zhongshan University, license number SCXK (Guangdong) 2011-0029. Prior to the experiment, the animals were housed in the quarantine room of SPF class animal room for one week, and were used for the first open-field test after quarantine pass. Animals were randomly divided into model group (n=60) and normal control group (n=10). Rats in the model group were individually kept in a single cage, i.e., 1 rat per cage; and rats in the normal control group were kept at 5 animal/cage. After 1 week of adaptive feeding, the model group rats were modeled by chronic Unpredictable Mild Stress (CUMS) for 3 weeks. The normal control group rats did not receive any irritation and were normally kept. After 3 weeks, 50 rats with compared results according to the test of sugar water consumption test were selected into the model and used in the second open-field test. Rats in the model group were randomly divided into model control group, positive control group, product 1 low dose group, product 1 medium group, product 1 high dose group (n=10), and individually kept in a single cage, i.e., 1 rat per cage.

2 Experimental Dose

Product 1 high dose group: 576 mg·kg$^{-1}$, prepared by grinding after adding distilled water;

Product 1 medium dose group: 288 mg·kg$^{-1}$, prepared by grinding after adding distilled water;

Product 1 low dose group: 144 mg·kg$^{-1}$, prepared by grinding after adding distilled water;

Rats in the positive control group were administered with imipramine 15 mg/kg, which was prepared by grinding after adding distilled water.

Rats in the model control group were administered with Distilled water 5 ml/kg.

3. Experiment Method

The experiment lasted for 12 weeks. The first week was for adaptive feeding, where rats of the model group and the normal control group were adequately fed and drunk; 2-4 weeks were for modeling of the model group by CUMS, where the rats in the model group were randomly administrated with at least one of the following stress daily: fasting (24 h), water deprivation (24 h), tail nipping (1 min), reversed day and night, wet litter (litter:water=1:1), tilting cage (45°), swimming in ice water (4° C., 5 min) and combined in a cage (5 animal/cage, 24 h), in which random stimulation was given to each rat every day, and the stimulations in two consecutive days cannot be the same, such that the rat cannot anticipate the type of the stimulation to be occurs, to avoid adaptation. After 3 weeks, 50 rats with compared results according to the test of sugar water consumption test were selected into the experiment model and used in the second open-field test. Rats in the model group were randomly divided into model control group, positive control group, product 1 high, medium and low dose groups, and were administrated from week 4 of modeling, in which the model control group was intragastrically administered with distilled water daily, the positive control group was intragastrically administered with imipramine at 15 mg/kg daily, and the high, medium and low dose groups were intragastrically administered with the Chinese herbal compound at the corresponding dose, respectively. Animals in each group were continuously administrated for 8 weeks, while continuing stimulation daily.

4. Observe Indicators 4.1 Sugar Water Consumption Test

Recorded the consumption (g) of 1% sugar water by the rats in each group and degree of preference for sugar water after the administration.

4.2 Forced Swimming Test

Recorded the swimming time (s) and the floating immobility time (s) within 4 min for rats in each group in the forced swimming test.

4.3 Tail Hanging Test

Recorded the accumulated immobility time (s) within the last 4 min in 6 min after the hanging test.

4.4 Data Statistics Processing

All data are the mean±standard deviation (mean±SEM). SPSS17.0 statistical software was used for data processing. Comparison between two groups was performed by using t-test for homoscedasticity, and using t'-test for heteroscedasticity. Comparison among multiple groups was performed using variance analysis for homoscedasticity, and using variance analysis after data conversion for heteroscedasticity, followed by LSD (homoscedasticity) or Dunnett's T3 (heteroscedasticity) multiple comparison. p<0.05 indicates having a statistical sense, p<0.01 indicates a significant statistical sense.

5 Experimental Results 5.1 Sugar Water Consumption Test 5.1.1 Sugar Water Consumption after Administration Before administration, that is, after modeling, the consumption of sugar water in each group of the model group was lower than that of the normal control group, and the difference has statistical sense (p<0.05); there is no statistical differences between the groups in the model group. After 2 weeks of administration, the consumption of sugar water in each group of the model group was lower than that of the normal control group, and the difference has statistical sense (p<0.05); the consumption of sugar water in product 1 medium and high dose group was higher than that of the model control group, and the difference has statistical sense (p<0.05). After 5 weeks of administration, the consumption of sugar water in the model control group was lower than the normal control group and each drug group, and the difference has statistical sense (p<0.05). After 8 weeks of administration, the consumption of sugar water in the model control group was still lower than the normal control group and each drug group, and the difference has statistical sense (p<0.05), while there was no statistical differences between the drug groups and the normal control group. Specific results were shown in Table 4.

TABLE 7

Comparison of the sugar water consumption by rats before and after administration ($\bar{x} \pm s$) (g)

| group | n | before ad. | 2 w after ad. | 5 w after ad. | 8 w after ad. |
|---|---|---|---|---|---|
| Normal control group | 10 | 8.03 ± 2.58# | 8.08 ± 1.08# | 8.14 ± 1.74# | 8.85 ± 2.27# |
| Model control group | 10 | 3.43 ± 1.59* | 3.35 ± 1.08* | 1.91 ± 0.97* | 2.76 ± 1.21* |
| Positive drug control group | 10 | 3.16 ± 1.85* | 5.40 ± 1.71* | 8.96 ± 1.80# | 9.03 ± 2.32# |
| Pro. 1 low dose group | 10 | 3.53 ± 2.41* | 5.11 ± 2.10* | 7.76 ± 1.23# | 8.30 ± 2.49# |
| Pro. 1 medium dose group | 10 | 2.84 ± 1.20* | 5.21 ± 0.71*# | 8.27 ± 0.55# | 8.80 ± 1.97# |
| Pro. 1 high dose group | 10 | 1.96 ± 1.79* | 5.06 ± 1.04*# | 8.47 ± 1.06# | 8.28 ± 2.22# |

Note:
*P < 0.05, vs. the normal control group;
P < 0.05, vs. the model control group.

5.1.2 the Degree of Preference for Sugar Water after Administration

Prior to administration, no significant difference in the degree of preference for sugar water was found. After 2 weeks of administration, the degree of preference for sugar water in the model control group was lower than that in the normal control group, positive control group, and product 1 medium dose group, and the difference has statistical sense (p<0.05); the degree of preference for sugar water in the product 2 low dose group was lower than that in the normal control group, and the difference has statistical sense (p<0.05). After 5 weeks of administration, the degree of preference for sugar water in the model control group was lower than that in the normal control group and each drug group, and the difference has statistical sense (p<0.05). After 8 weeks of administration, the degree of preference for sugar water in the model control group was lower than that in the normal control group and each drug group, and the difference has statistical sense (p<0.05), while there was no statistical differences between each drug group and the normal control group. Specific results were shown in Table 5.

TABLE 8

Comparison of the degree of preference for sugar water for the rats before and after administration ($\bar{x} \pm s$) (%)

| group | n | before ad. | 2 w after ad. | 5 w after ad. | 8 w after ad. |
|---|---|---|---|---|---|
| Normal control group | 10 | 63.39 ± 21.75 | 72.17 ± 13.85# | 79.25 ± 8.03# | 72.85 ± 8.61# |
| Model control group | 10 | 64.04 ± 17.72 | 50.57 ± 20.78* | 24.16 ± 12.52* | 46.11 ± 27.14* |
| Positive drug control group | 10 | 49.16 ± 29.66 | 71.29 ± 20.39# | 77.81 ± 12.49# | 73.14 ± 18.10# |
| Pro. 1 low dose group | 10 | 52.76 ± 29.77 | 55.95 ± 17.89* | 72.54 ± 14.52# | 78.47 ± 16.26# |
| Pro. 1 medium dose group | 10 | 53.72 ± 23.23 | 72.60 ± 11.61# | 72.11 ± 7.87# | 72.90 ± 10.75# |
| Pro. 1 high dose group | 10 | 41.55 ± 29.02 | 56.96 ± 18.01 | 74.26 ± 13.06# | 70.31 ± 12.27# |

Note:
*P < 0.05, vs. the normal control group;
P < 0.05, vs. the model control group.

5.2 Forced Swimming Test

Compared with the model control group, before administration, there was no significant difference in the immobility time in swimming between each drug group and the model control group; after administration, the immobility time in swimming of each drug group was reduced and lower than that of the model control group, and the difference has statistical sense (p<0.05). Furthermore, as the increase of dose of the Chinese herbal compound, the swimming immobility time has a tendency to reduce. Specific results were shown in Table 6.

TABLE 9 change in the swimming immobility time before and after administration ($\bar{x} \pm s$)(s)

| group | n | before ad. | after ad. |
|---|---|---|---|
| Normal control group | 10 | 42.30 ± 8.23# | 42.65 ± 14.34# |
| Model control group | 10 | 79.35 ± 14.34* | 96.25 ± 17.35* |
| Positive control group | 10 | 82.40 ± 17.72* | 35.33 ± 6.61# |
| Pro. 1 low dose group | 10 | 78.25 ± 17.65* | 41.75 ± 9.13# |

TABLE 9-continued change in the swimming immobility time before and after administration ($\bar{x} \pm s$)(s)

| group | n | before ad. | after ad. |
|---|---|---|---|
| Pro. 1 medium dose group | 10 | 79.90 ± 24.87* | 35.00 ± 9.60# |
| Pro. 1 high dose group | 10 | 83.70 ± 26.35* | 32.50 ± 8.10# |

Note:
*P < 0.05, vs. the normal control group;
P < 0.05, vs. the model control group.

5.3 Tail Hanging Test

Compared with the model control group, before administration, there is no significant difference in the immobility time in hanging between each drug group and the model control group; after administration, the immobility time in swimming of each drug group is reduced and lower than that of the model control group, and the difference has statistical sense (p<0.05). Specific results were shown in Table 7.

TABLE 10 change in the hanging immobility time before and after administration ($\bar{x} \pm s$) (s)

| group | n | before ad. | after ad. |
|---|---|---|---|
| Normal control group | 10 | 95.20 ± 21.68# | 104.90 ± 16.03# |
| Model control group | 10 | 173.00 ± 32.88* | 173.40 ± 21.60* |
| Positive control group | 10 | 189.50 ± 30.88* | 116.60 ± 21.06# |
| Pro. 1 low dose group | 10 | 170.70 ± 26.82* | 113.90 ± 15.20# |
| Pro. 1 medium dose group | 10 | 189.50 ± 16.80* | 107.00 ± 28.21# |
| Pro. 1 high dose group | 10 | 173.50 ± 19.75* | 107.00 ± 34.93# |

Note:
*P < 0.05, vs. the normal control group;
P < 0.05, vs. the model control group.

Depression refers to a mood disorders syndrome with main clinical manifestations of low mood, slow thinking and reduced interest and initiative and other psychomotor retardation symptoms. It has been reported that, the rat model of depression produced by separately feeding in combination with long-term unpredictable moderate-intensity stress shown a series of emotional behavior changes and had a certain degree of similarity to human depression, leading to symptoms of experimental animals such as lack of pleasure, lack of interest, mental retardation and so on. The modeling effect of CUMS and the antidepressant effect of the Chinese herbal compound on the CUMS depression rats can be determined by the results of open-field test, sugar water consumption test, forced swimming test and tail hanging test.

In summary, continuous CUMS procedures can cause the lack of pleasure in rats, reflected as reduced sugar water consumption, suggesting that CUMS depression model was modeled successfully. After continuous administration of the plant extracts for soothing the liver for 8 weeks, the depressive symptoms of CUMS depression rats were improved to some extent, and have a trend towards the normal control group, reflected as the consumption of sugar water in the drug group being higher than that in the model control group, and the reduced immobility time in the forced swimming and tail hanging compared with the model control group ($p<0.05$). Therefore, the Chinese herbal compound can be considered having antidepressant effect in a certain extent.

The above experiments were repeated using the products obtained in Examples 2 to 10, and similar experimental results were obtained, and the description thereof will not be repeated here.

In sum, the present inventor according to the theoretical basis of Chinese medicine for a breast disease such as breast hyperplasia and depression, supplemented by the compatibility of Chinese medicine, finds a formulation and preparing method of a Chinese herbal medicine composition, which overcomes the disadvantages, for example, too many herbs, complicated preparation process, large administration dose, unsuitable for long-term use and poor consumer compliance, of the existing Chinese medicine prescription product for breast diseases such as breast hyperplasia and the like, as well as the lack of Chinese medicine products for relieving depression. The invention initiates a Chinese medicine product which can simultaneously treat the breast disease and alleviate the depression, and has a milestone significance for the research and development of the Chinese medicine product.

The foregoing is only a preferred embodiments of the present invention and it should be noted that several modifications and changes may be made by those skilled in the art without departing from the principles of the invention, and these modifications and changes should be regarded as within the scope of protection of the present invention.

The invention claimed is:

1. A method for preparing a Chinese herbal medicine composition for soothing the liver, comprising:
    Step 1, extracting: adding a first amount of a solvent to a mixture of 20-50 parts by weight of *Rhizoma Cyperi*, 10-30 parts by weight of *Radix Angelicae Sinensis*, 10-30 parts by weight of *Rhizoma Ligustici Chuanxiong*, 5-20 parts by weight of *Radix Paeoniae Alba*, and 5-20 parts by weight of *Pericarpium Citri Reticulatae* to perform a first extraction, filtering and collecting a first filtrate; adding a second amount of the solvent to perform a second extraction, filtering and collecting a second filtrate; combining the first filtrate and the second filtrate to obtain an extract;
    Step 2, concentrating: concentrating the extract under reduced pressure to give a concentrated product;
    Step 3, drying; and
    mixing the product obtained after drying with 0.5-10 parts by weight of a green tea extract,
    wherein the mass ratio of the first amount of the solvent to the mixture is (9-12):1, the extraction time of the first extraction is 1 to 3 hours, and the extraction condition of the first extraction is in boiling; the mass ratio of the second amount of the solvent to the mixture is (7-10):1, the extraction time of the second extraction is 0.5 to 1.5 hours, and the extraction condition of the second extraction is in boiling; the solid content of the concentrated product is 20 to 30%.

2. The method according to claim 1, further comprising preparing the product obtained after drying into an oral preparation in a dosage form selected from one or more of oral liquid, powder, granule, tablet and capsule.

3. The method according to claim 1, wherein:
    the weight of *Rhizoma Cyperi* is 30 g, the weight of *Radix Angelicae Sinensis* is 20 g, the weight of *Rhizoma Ligustici Chuanxiong* is 20 g, the weight of *Radix Paeoniae Alba* is 10 g, and the weight of *Pericarpium Citri Reticulatae* is 10 g;
    the solvent is water, and the first amount of water is 0.9 kg, the second amount of water is 0.72 kg;
    the extraction time of the first extraction is 1.5 h, and the extraction time of the second extraction is 1 h;
    the solid content of the concentrated product is 20%; and
    the weight of the green tea extract is 2 g.

* * * * *